United States Patent [19]

Carle et al.

[11] Patent Number: 5,244,885
[45] Date of Patent: Sep. 14, 1993

[54] CAMOMILE EXTRACT HAVING ANTIMICROBIAL PROPERTIES, PROCESS FOR ITS MANUFACTURE AND ITS USE

[75] Inventors: Reinhold Carle, Rödermark; Claus Gehringer, Frankfurt; Jürgen Beyer, Ludwigshafen; Jürgen Engel, Alzenau, all of Fed. Rep. of Germany

[73] Assignee: Asta Medica Aktiengesellschaft, Fed. Rep. of Germany

[21] Appl. No.: 820,407

[22] Filed: Jan. 15, 1992

[30] Foreign Application Priority Data

Jan. 23, 1991 [DE] Fed. Rep. of Germany ....... 4101826

[51] Int. Cl.$^5$ .................. A61K 31/70; A61K 31/35

[52] U.S. Cl. ................................ 514/25; 514/456; 514/729

[58] Field of Search ............. 424/195.1; 514/456, 514/729, 25

[56] References Cited

U.S. PATENT DOCUMENTS 4,786,498 11/1988 Isaac et al. ............... 424/195.1

*Primary Examiner*—John W. Rollins
*Attorney, Agent, or Firm*—Cushman, Darby & Cushman

[57] ABSTRACT

A process for the preparation of a polar, antimicrobially active camomile extract by extraction of camomile ligular florets using conventional camomile extraction agents and optionally subsequent spray-drying.

2 Claims, No Drawings

CAMOMILE EXTRACT HAVING ANTIMICROBIAL PROPERTIES, PROCESS FOR ITS MANUFACTURE AND ITS USE

The present invention relates to a hydrophilic extract predominantly composed of camomile ligular florets that may, for example, be used for liquid vaginal preparations for human females. For use as a vaginal douche it is also possible to add or use additives conventionally known for pharmaceutical compositions intended for this use.

BACKGROUND OF THE INVENTION

Vaginal douches are liquid preparations for douching the vagina for an indeterminate period to achieve a cleaning, soothing and refreshing effect, to eliminate odor, to relieve slight irritation, to reduce the number of pathogenic microorganisms, to change the pH and hence stimulate the growth of a normal vaginal flora, to achieve an astringent effect, and to reduce the surface tension to achieve a mucolytic or proteolytic effect. Vaginal douches are frequently used for intravaginal contraception. They have also been proposed as a method for influencing the sex of a baby by using acid or basic douches before coitus (SHETTLES, L.B. (1970): Intern. J. Gynaecol. Obstetrics 8.643).

The antiseptic properties of the plant-containing essential oil are generally attributed to the volatile compounds contained therein (TYLER, V.E. et al.: Pharmacognosy, 7th Edition, Lea-Febiger, Philadelphia 1976, p. 137). In low concentrations, camomile oil has a bacteriostatic and bactericidal effect on gram-positive pathogens and is characterized by a remarkable fungicidal effect against Candida albicans (AGGAG, E. and T. YOUSEF (1972): Planta Med. 22, 140). In vivo tests to compare the lipophilic constituents of camomile florets have shown ($-$)-alpha-bisabolol to have the strongest bacteriostatic effect (SZABO-SZALONTAI et al. (1975): Pharm. Ztg. 120, 982; Dtsch. Apoth. Ztg. 115. 912).

It has been reported that a non polar fraction obtained from camomile florets has an inhibitory effect on the growth of microorganisms isolated from the vaginal secretion. In this case the camomile florets were extracted with ethanol under reflux, the extract was filtered, and the solvent was evaporated. The pasty residue was then worked up several times with cold hexane. The residue was dissolved in hot methanol, filtered and the solution evaporated to dryness. This extract does not contain any flavones and shows no bacteriostatic effect (TURBARO, A. et al.; Europ. Pat. App. No. 0096016 dated Jun. 1, 1983).

The ligular florets of camomile mainly contain flavones, for example apigenin-7-glucoside, apigenin-7-acetyl glucoside and apigenin and other polar compounds. Volatile constituents (=essential oil) of the camomile are mainly found in the tubular florets of the flower head, whereas only small amounts thereof have been found in the ligular florets.

SUMMARY OF THE INVENTION

It has now surprisingly been found that a fraction obtained from camomile ligular florets by extraction with hot water has a substantial bacteriostatic and trichomonacidal action. This fraction has totally unexpectedly displayed a bacteriostatic action, although it consists exclusively of polar compounds, for example flavones, flavone glycosides and polysaccharides.

The bacteriostatic action of preparations composed of this camomile fraction and of combinations with other effective substances wa determined using the standard method of serial dilution in a liquid and subsequent determination of the number of viable organisms on a solid culture medium (MEINGASSNER et al. (1981): Arzneim. Forsch. 31, 6). Isolates of vaginal microorganisms were used for the antibacterial tests.

The determination was conducted for example in the following manner:

An isolate of vaginal microorganisms was transferred to an agar culture medium, cultured for 24 hours at 37° C. and transferred to a liquid medium using sterile water. The liquid culture medium used as inoculum contained $10^4$ microorganisms per ml. 10 ml portions of it were dispensed into 200 ml bottles. The camomile extract was added in various concentrations to these samples (1 to 10 mg/ml). After incubation for 24 hours at 37° C. the number of surviving microorganisms was determined.

The growth of an isolate of vaginal microorganisms was 100% inhibited by 5 mg/ml (Mar. 5, 1990).

The present invention therefore relates to an extract of camomile florets having a bacteriostatic and trichomonicidal action which may be obtained by extracting camomile ligular florets. It also is possible to use smaller amounts of camomile tubular florets in addition to the camomile ligular florets, up to a maximum of 0.3 parts by weight of tubular florets to one part by weight of ligular florets.

The present invention also provides a process for making the foregoing isolate from camomile ligular florets, or mixtures of camomile ligular florets with smaller amounts of camomile tubular florets, up to a maximum of 0.3 parts by weight of tubular florets to one part by weight of ligular florets. In accordance with the method of the invention, the florets are extracted with at least one organic polar solvent which is miscible with water and having a boiling point between 30 and 90° C. or mixtures of one or more such solvents with water at temperatures between 60°-100° C. The florets are extracted for at least one minute and, optionally, the extraction solvent is then removed.

The invention also provides a method of using of an extract of this kind as a vaginal douche as well as appropriate pharmaceutical formulations containing this extract.

In particular a formulation of this kind is a pale yellow aqueous solution having a pH value between 3.0 and 4.0, a specific gravity of 1.0004–1.0006 containing the polar camomile constituents apigenin, apigenin-7-glucoside and apigenin-7-acetyl glucoside with a total flavonoide content between 1 and 30 mg/ml, 0.1–3.0% by weight of a physiologically acceptable buffer for adjusting the pH to a value between 3.0 and 4.0 as well as optionally other physiologically and pharmaceutically acceptable auxiliary substances, preservatives, fragrances, aromatic and/or coloring agents.

The manufacture of a vaginal douche formulation of this type is carried out, for example, using the extract of the invention, by spray-drying the extract, optionally with or without conventional auxiliary substances, dissolving the product thereby obtained in water, mixing the product obtained with physiologically acceptable pharmaceutical auxiliary substances and additives, filtering, sterilizing and filling under aseptic conditions.

PREPARATION OF THE CAMOMILE EXTRACT OF THE INVENTION

The main starting materials are ligular florets of camomile. It is possible to use fresh or dried florets. In the case of dried florets, these are always florets that are dried at 20° to 60° C. until they reach constant weight (drying occurring for example at 40° C.).

Dried florets useful for the invention contain a maximum of up to 25% percent by weight of water.

When fresh material is used, the amount of starting material must be five times greater than for dried material. During extraction of the ligular florets it is optionally also possible to use in addition smaller amounts of camomile tubular florets. Instead of dried florets it is in each case also possible to use the corresponding drug equivalent in fresh florets (ligular florets and/or tubular florets).

If using mixtures of ligular florets and tubular florets, these are composed as follows:

A maximum of up to 0.3 parts by weight of dried camomile tubular florets may be used to 1 part by weight of dried camomile ligular florets (i.e. 0–0.3 parts by weight of camomile tubular florets).

If fresh camomile tubular florets are used, the ratio of 0–0.3 parts by weight of fresh tubular florets to one part by weight of fresh ligular florets also applies for the proportion of fresh tubular florets.

When fresh camomile ligular florets and dried camomile tubular florets are used, 0–0.1 parts by weight of dried camomile tubular florets are preferably used to one part by weight of fresh camomile ligular florets (drying always as stated above).

When dried camomile ligular florets and fresh camomile tubular florets are used, 0–1.5 parts by weight of fresh camomile tubular florets are preferably used to one part by weight of dried ligular florets.

The extraction agent may for example be a liquid solvent with a boiling point between 50° and 150° C., preferably 56° and 120° C., in particular 56° and 105° C. Examples of such agents are: water, primary, secondary or tertiary mono- or multivalent saturated aliphatic alcohols such as methanol, ethanol, propanol, isopropanol, aliphatic saturated ketones with 1–4 carbon atoms (acetone, methyl ethyl ketone) or mixtures of these agents.

The extraction temperature is for example between 60° and and 100° C., preferably 70° to 100° C., in particular 90° to 100° C.

The extraction is carried out for example in the apparatus or devices conventionally used for camomile extractions. It is for example possible to proceed as follows:

To one part by weight of fresh ligular florets for example 2 to 10, preferably 4 to 8, in particular 4 to 6 parts by weight of the previously mentioned extraction agent(s) are used.

To one part by weight of dry ligular florets, 10 to 60, preferably 20 to 50, in particular 20 to 40 parts by weight of the previously mentioned extraction agent(s) are used. These amounts of extraction agents also apply if tubular florets are used in addition to the ligular florets, regardless of whether the tubular florets are dried or fresh florets.

The extraction time is for example 1 to 15, preferably 3 to 10, in particular 3 to 5 minutes.

After extraction, the extracted material is for example passed through a press, is filtered and spray-dried, optionally using conventional auxiliary substances and additives such as lactose and cellulose derivatives.

During spray-drying it is for example also possible to use other substances conventionally used for this purpose.

The dry extract obtained in this manner is then suitable for the manufacture of therapeutic compositions (for example for a vaginal douche). The solubility of the spray-dried extract obtained in this manner is best in water (1 part of the extract dissolves for example in approximately 5 parts of water) and decreases with decreasing polarity of the solvent.

Other solvents for the extract are physiologically acceptable solvents of a polar nature, such as alcohols with chain lengths of up to 6 carbon atoms.

The therapeutic compositions (vaginal douche for example) are, e.g., obtained by dissolving the spray-dried extract in purified water, the pH being adjusted to a value of 3.0 to 4.0 using lactic acid/sodium lactate (for example using a mixture of lactic acid and sodium lactate in a ratio of 2 to 1). The concentration of the lactic acid/sodium lactate mixture is for example 0.1 to 3.0 percent by weight, preferably 0.4 to 1.3 percent by weight.

Other conventional buffers may also be used to adjust to a pH value of 3.0 to 4.0.

Other conventional additives or auxiliary substances conventionally used in vaginal douches may optionally be added to the therapeutic formulations.

The following substances may for example be used as additives of this nature:

(The following percentages by weight relate in each case to the finished final composition).

Alkali metal salts or alkaline earth metal salts of propionic acid, such as calcium or sodium propionate, for example in concentrations up to 20% by weight, alkali metal salts of sorbic acid, such as potassium sorbate (for example in concentrations between 1 and 3%), polyvinylpyrrolidoneiodide (concentrations for example between 0.1 and 0.3% by weight), sodium benzoate, benzoic acid, sodium citrate.

These are preferably physiologically acceptable substances having a favorable influence on mucous membrane irritation.

It is also possible to consider surface-active substance such as anionic and non-ionic detergents. Anionic detergents that may for example be used are dioctyl sodium sulfosuccinate or sodium lauryl sulfate (concentrations between 0.002 and 0.02% by weight): dioctyl sodium sulfosuccinate preferably in an amount of 0.002 to 0.01% by weight; sodium lauryl sulfate preferably in an amount of 0.01–0.02% by weight.

Nonionic detergents that may for example be considered are octoxynol-9 and/or nonoxynol-9 (concentrations between 0.01% by weight and 0.1% by weight). Octoxynol-9 preferably in the concentration from 0.08 to 0.09% by weight; nonoxynol-9 preferably in the concentration 0.01 to 0.02% by weight.

To change the vaginal pH value and to encourage normal growth of the vaginal flora, it is possible to use acetic acid between 4 and 6% by weight as well as boron compounds such as boric acid, sodium borate, sodium perborate and glycerin of boric acid in concentrations between 0 and 1.0% by weight, citric acid between 0.1 and 0.5%, lactic acid or alkali metal salts of lactic acid, in particular sodium lactate or mixtures of sodium lactate and lactic acid with a total content of 0.4 to 3.0% by weight, sodium bicarbonate, sodium carbonate and/or tartaric acid (concentration in each case from 0.02 to 3.0% by weight).

Astringent agents that may be contained in the pharmaceutical formulations (vaginal douche) of the invention are for example aluminum compounds such as potassium aluminum sulfate, ammonium aluminum sulfate (0.03 and 0.06% by weight), boron compounds such as boric acid, sodium borate, sodium perborate and glyceride of boric acid, zinc sulfate (in each case 0.001 to 0.02% by weight).

In addition the pharmaceutical formulations of the invention may also contain mucolytic and proteolytic substances such as: alkyl aryl sulfonates (concentrations up to 0.1% by weight), lactic acid, alkali acetate, papain (concentration in each case 0.005 to 0.1% by weight).

Auxiliary substances and additives that may preferably be used are: octoxynol-9 (content for example 0.08 to 0.1% by weight) and/or nonoxynol-9 (content for example 0.01% by weight) as well as sodium benzoate (content for example 0.1 to 0.5% by weight).

The previously mentioned additives may be used singly or also in combination.

Other additives that may for example be used are: fragrances and/or aromatic agents and colorants which are used in each case in the appropriate permissible substance-specific concentrations. In the case of the fragrances the concentration is generally under 1% by weight.

The composition obtained in this manner (vaginal douche) is then for example filtered through a filter of pore size 0.1 to 2 $\mu$m, preferably 0.22 $\mu$m, sterilized with steam at 120° C. for 20 minutes and dispensed into the final packaging under sterile conditions.

DETAILED DESCRIPTION OF PREFERRED EMBODIMENTS

The invention is illustrated by the following examples:

EXAMPLE 1

A mixture of 3.750 kg ligular florets and 0.425 kg tubular florets is extracted with 125 kg water for 10 minutes at 90° C. 125 kg of the filtered extract is atomized in a direct current spray-drying apparatus at a pressure ($1.3 \times 10^5$ Pa). The inlet temperature of the drying air is 140° C. and the outlet temperature is 90° C. 0.75 kg of spray dried product is obtained. After adding 873.00 kg purified water, 3.50 kg lactic acid 90% and 4.63 kg sodium lactate 50% are dissolved into the aqueous mixture so obtained. The mixture is then filtered, sterilized and filled under aseptic conditions.

EXAMPLE 2

A mixture of 3.750 kg ligular florets and 0.425 kg tubular florets is extracted with 125 kg water for 10 minutes at 90° C. The filtered extract supplies 0.75 kg of the spray-dried product. After adding 873.00 kg purified water, 3.50 kg lactic acid 90% and 2.10 kg sodium lactate 50%, 0.77 kg octoxynol-9 and 1.31 kg sodium benzoate are dissolved into the aqueous mixture so obtained. The mixture is then filtered, sterilized and dispensed into the final packaging under aseptic conditions.

EXAMPLE 3

A mixture of 3.550 kg ligular florets and 0.625 kg tubular florets is extracted with 125 kg water for 15 minutes at 95° C. The filtered extract supplies 0.80 kg of the spray-dried product. After adding 931.00 kg purified water, 3.73 kg lactic acid 90% and 2.24 kg sodium lactate 50%, 0.82 kg octoxynol-9 and 1.40 kg sodium benzoate are dissolved into the aqueous mixture so obtained. The mixture is then filtered, sterilized and dispensed into the final packaging under aseptic conditions.

What is claimed is:

1. A weakly yellow aqueous solution having a pH value between 3.0 and 4.0, a specific gravity of 1.0004–1.0006 containing the polar camomile constituents apigenin, apigenin-7-glucoside and spigenin-7-acetyl glucoside with a total flavonoide content between 1 and 30 mg/ml, 0.1–3.0% by weight of a physiologically acceptable buffer for adjusting the pH value between 3.0 and 4.0 as well as optionally other physiologically acceptable auxiliary substances, preservatives, fragrances, aromatic and/or coloring agents.

2. A method of cleansing the vagina which comprises applying thereto the composition of claim 1.

* * * * *